(12) United States Patent
Penu et al.

(10) Patent No.: US 9,777,109 B2
(45) Date of Patent: Oct. 3, 2017

(54) PROCESS FOR PRODUCING POLYLACTIDE

(71) Applicant: FUTERRO S.A., Escanaffles (BE)

(72) Inventors: Christian Penu, Saint Saulve (FR);
Philippe Coszach, Escanaffles (BE);
Marie-Astrid Feron, Erbisoeul (BE);
Arnaud Delrue, Piéton (BE)

(73) Assignee: Futerro S.A., Escanaffles (BE)

( * ) Notice: Subject to any disclaimer, the term of this patent is extended or adjusted under 35 U.S.C. 154(b) by 0 days.

(21) Appl. No.: 15/102,812

(22) PCT Filed: Dec. 9, 2014

(86) PCT No.: PCT/EP2014/077076
§ 371 (c)(1),
(2) Date: Jun. 8, 2016

(87) PCT Pub. No.: WO2015/086613
PCT Pub. Date: Jun. 18, 2015

(65) Prior Publication Data
US 2016/0311971 A1    Oct. 27, 2016

(30) Foreign Application Priority Data

Dec. 10, 2013 (EP) ..................................... 13196404

(51) Int. Cl.
*C08G 63/08* (2006.01)
*C08G 63/78* (2006.01)
*C07C 59/08* (2006.01)

(52) U.S. Cl.
CPC ............ *C08G 63/08* (2013.01); *C08G 63/78* (2013.01); *C07C 59/08* (2013.01)

(58) Field of Classification Search
CPC ......... C07C 59/08; C07C 69/68; C08G 63/08; C08G 63/78
See application file for complete search history.

(56) References Cited

U.S. PATENT DOCUMENTS 6,326,458 B1 * 12/2001 Gruber ................. C07D 319/12
525/415
2006/0014975 A1    1/2006 Coszach et al.
2013/0267675 A1 * 10/2013 Yoshida ................... B01D 1/22
528/361

FOREIGN PATENT DOCUMENTS

EP        2607399 A1    6/2013

* cited by examiner

*Primary Examiner* — Gregory Listvoyb
(74) *Attorney, Agent, or Firm* — Reinhart Boerner Van Deuren P.C.

(57) ABSTRACT

The present invention relates to an improved process for producing polylactide where the goal is to recover a maximum of useful matters in order to recycle without loss and so significantly improving the global yield of the production process of polylactide when starting from lactic acid.

8 Claims, 1 Drawing Sheet

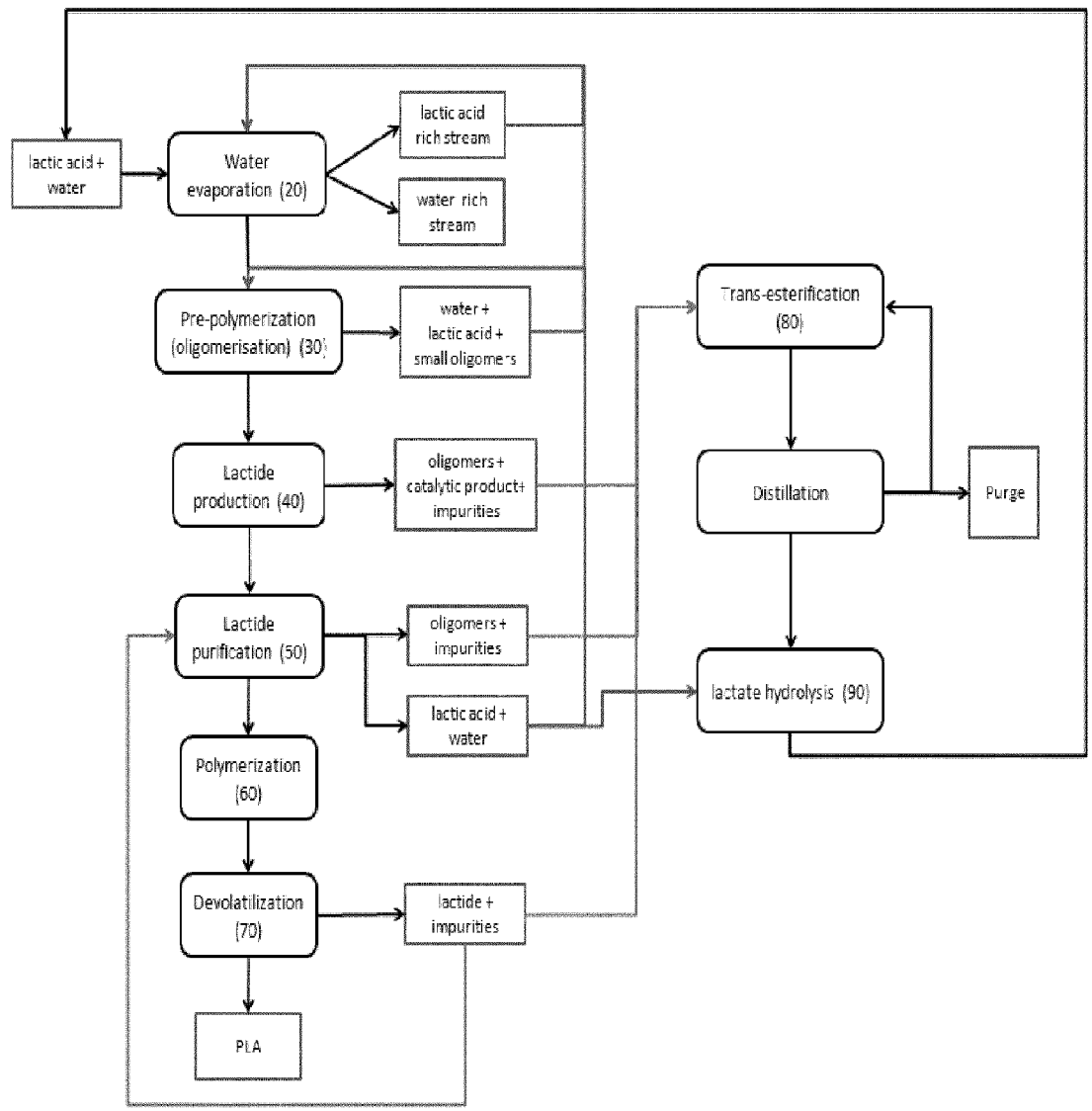

PROCESS FOR PRODUCING POLYLACTIDE

The present invention relates to a process for the production of polylactide (PLA). Particularly, the present invention relates to an improved process where the goal is to recover a maximum of useful matters in order to recycle without loss and so significantly improving the global yield of the production process of PLA when starting from lactic acid.

BACKGROUND

Mainly two types of process have been described for the production of PLA; the first one consists in a direct polycondensation of lactic acid, as described for instance in JP patent 733861; such type of process is limited by the use of a solvent and the difficulty of removing water out of the reaction medium.

It is well known that in a second type of usual process for producing PLA starting from lactic acid, a significant loss of products, including lactic acid, lactide, oligomers of lactic acid and similar, occurs at each step of the global polymerization process; such steps may be summarized as follows: (i) oligomerization of lactic acids into oligomers, (ii) cyclization of the oligomers into lactide species, (iii) purification of lactide to obtain a suitable grade to start the last step which is the polymerization by ring opening of the purified lactide. Of course after this last step a devolatilization shall take place to recover the non-converted lactide.

Depending of the various processes for the production of PLA, it may be said that a lot of matters are lost all along the achievement of the process, so decreasing considerably the overall yield of said process. Indeed, if we take as a reference, a theoretical process without any recycling, the overall yield is as low as about 50% (molar).

It was therefore envisioned in the past to control certain partial recycling of streams issued from the step of evaporation of water from the starting lactic acid aqueous solution, from the step of oligomerization and from the step of the cyclization reaction; with such recycling operations, the overall yield has reached values as high as 75% (molar); however, even with those efforts which have been made and described to recover and finally recycle such type of lost product, this is not yet satisfactory to conduct an industrial process.

Therefore, there is a need for a process which enables not only to drastically reduce such loss of products, but mainly to incorporate in a global process the implementation of the recovery of the lost products and a process to convert such products to the starting monomer or its derivatives.

Therefore, the object of the present invention is to provide a process for the production of PLA wherein the recovery of the oligomers of lactic acid, lactide, and catalytic residues as well are implemented in order to treat and convert them into the starting monomer or its derivatives.

Another object is to recover the residues at each step of the process.

A further object is to treat the residues of lactic acid oligomers.

Another object is to implement the recovery and the recycle of the streams of lactic acid and water.

Another object is to provide a trans-esterification process to convert the oligomers residues with an alcohol.

Finally the process of the invention should also provide for treating the formed lactate compounds by hydrolysis in order to recover the alcohol and the lactic acid or its derivatives.

At least one of these objectives is met by the process of the invention.

DETAILED DESCRIPTION

The process of the present invention is also described in view of the accompanying drawings where FIG. 1 is representing the global flow sheet of a process for the production of PLA with the recovery steps and conversion steps to the starting monomer.

DESCRIPTION OF THE GLOBAL PROCESS

The present invention provides an integrated process for the production of polylactide (PLA) comprising the steps of:
(1) Water evaporation from the lactic acid aqueous solution starting stream;
(2) Oligomerization of lactic acid and recycle of reaction water and unconverted lactic acid;
(3) Cyclization of the lactic acid oligomers and production of crude lactide and recycle of unreacted monomers, catalytic residues and heavy products;
(4) Purification of the crude lactide and recycle of lactic acid, water, heavy components, catalytic residues and impurities;
(5) Ring opening polymerization of the purified lactide and production of PLA;
(6) Purification of the PLA by devolatilization and recycle of non-reacted lactide;
wherein
recycle of step (2) comprises water, which is purged, and lactic acid which is recycled to reactor (20);
recycle of step (3) is sent to trans-esterification reactor (80);
recycle of step (4) comprising (i) the light components, is sent to reactor (20) the other part to the hydrolysis reactor (90), and (ii) the heavy components stream is sent to trans-esterification reactor (80);
recycle of step (6) is sent partially to step (4) and the rest is sent to trans-esterification reactor (80).

The first step of the process to produce PLA consists in the removal of water from the starting aqueous solution of lactic acid (from 50 to 100% concentration) and the second step consists in the oligomerization of the lactic acid monomers into oligomers of low viscosity and molecular weight, generally comprised between 400 and 5,000 Dalton, in presence or not of a catalyst like for example a tin based catalyst. Typical temperature and pressure range for these two steps are respectively 100° C. to 200° C. and 5 mbara to 500 mbara. The molecular weight was measured by chromatography by gel permeation compared to standard polystyrene in chloroform at 30° C.

From these first and second steps, the process of the invention provides for the recovery of water, non-reacted lactic acid, oligomers of lactic acid.

The Applicant has noted that the residues of water and lactic acid are relatively pure, and therefore may be directly recycled to the evaporation step or the oligomerization step.

The Applicant has found that such a recycling of lactic acid could represent up to 5-15% by weight of the incoming lactic acid stream.

The oligomers coming from the step of oligomerization are then sent to the cyclization step which consists of treating the oligomers in a cyclization reactor, in the presence of a usual catalyst for such reaction like a tin based catalyst. From this third step, and besides the obtained crude lactide stream which will be sent to the purification, it is necessary to recover the unreacted oligomers, the non volatile impurities, the high boiling point lactic acid oligomers, the low molecular weight polylactic acid, having a molecular weight comprised between 2,000 and 8,000 Dalton, as well as the heavy residues and the catalytic residues which all form the cyclization residues. Typical temperature and pressure range for this step are respectively 200° C. to 320° C. and 5 mbara to 80 mbara.

These cyclization residues are sent back to the oligomerization step. However it is important to note that in order to avoid dramatic accumulation of catalytic residues in the system as well as degradation by-products, a purge is absolutely needed, which also contribute to the elimination of impurities giving rise to unwanted color. The products of the purge are then sent to the trans-esterification reactor (80).

During the fourth step, which is the purification of the crude lactide stream which may comprise different types of purification units like distillation means, crystallization means and analogs, it is recovered a light components stream containing lactic acid and water which is divided into two sub-streams, the first, representing from 10 to 100% by weight of the light components stream, is sent to the hydrolysis reactor (90) while the second, representing from 0 to 90% by weight of the light components stream, is recycled to reactor (20), while a bottom stream, containing heavy oligomers, lactide and impurities constituting stream will be recycled to the trans-esterification reactor (80).

The purified lactide is finally sent to the step of polymerization by ring opening to form PLA, having a molecular weight comprised between 10,000 and 200,000 Dalton.

This polymerization step is followed by a devolatilization step to purify the obtained PLA and to recover unreacted monomers and diluents as well as impurities.

The Applicants have now found that by operating the improved process of the invention, which comprises the steps of the water evaporation, oligomerization, crude lactide production, purification of the crude lactide, polymerization of the purified lactide by ring opening (ROP), devolatilization and the recovery of PLA, the improvement consists in:
  (i) recovery water and lactic acid in steps evaporation, oligomerization, cyclization and purification, and sent them back to step of evaporation and/or oligomerization,
  (ii) recovery of oligomers of lactic acid, lactide, catalytic residues of steps cyclization, purification, and devolatilization and sent them back to a trans-esterification reactor, where a trans-esterification reaction shall take place, and finally
  (iii) send the so formed alkyl lactate to a hydrolysis step to recover the starting monomer.

According to the process of the present invention, the trans-esterification reaction may be operated in accordance with known processes and under usual conditions; such a reaction may be achieved in one or more than one reactors at a temperature comprised between 80 and 200° C. and at a pressure comprised between the atmospheric pressure and 10-50 bara and in the presence of a catalyst.

According to one embodiment of the process of the present invention, the recycle stream from cyclization (noted step (3)) and the heavy components recycled from lactide purification (noted step (4)) and the part of stream coming from devolatilization (noted step (6)) are collected and sent to the trans-esterification reactor (80) where the trans-esterification reaction is conducted in one or more than one continuous stirred reactors working at a temperature ranging between 80 and 200° C., preferably between 100 and 180° C. and at pressure ranging between 1 and 20 bara, preferably between 2 and 15 bara, and finally the recovery of a stream comprising alkyl lactate which is sent to the hydrolysis reactor (90).

Generally the catalyst is at least partially supplied with the flow recovered from the cyclization step coming from the production of crude lactide stream.

With the trans-esterification reaction an alkyl lactate is formed and recovered which is further sent to a hydrolysis step to finally recover the starting monomer.

Before being sent to the hydrolysis reaction, the crude alkyl lactate exiting the reactor (80) is first purified in order to separate the lactate molecules from the heavier molecules. With this purification step, it is generally expected to recover substantially 80 to 100% of the lactate molecules, based on the fed lactate molecules. Usually, to achieve such a separation, the mixture coming out of the trans-esterification reactor (80) is first sent to a distillation step operated under pressure of 0.01 to 4 bara preferably between 0.1 to 1 bara and at a temperature comprised between 40 to 180° C., preferably between 60 to 150° C., said distillation step comprising one or more than one distillation columns or equivalent apparatus, where it is recovered at one side, the light components like lactate molecules which are then sent to the hydrolysis and on the other side the heavy components such as the catalytic residues, oligomers and the unreacted products, which are partially recycled to reactor (80) for trans-esterification and the rest is purged and optionally treated for example by filtration or decantation to separate the catalytic residues from the oligomers. These catalytic residues can be sent back to trans-esterification and/or oligomerization and/or cyclization reactors as such or with an additional treatment (e.g. drying).

The hydrolysis reactor (noted 90) is receiving, after distillation, the stream from the trans-esterification reactor as well as the part of light components coming from the purification of lactide and which is directly sent to the hydrolysis reactor. The hydrolysis reactor is then operated in accordance with the usual process to achieve such reaction and in accordance with usual conditions.

The hydrolysis reaction may be summerized as follows:

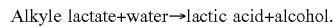

Alkyle lactate+water→lactic acid+alcohol.

According to one embodiment of the present invention, this type of reaction is achieved either in batch or continuously, and the reactor for such reaction may be realized generally in a reactive distillation column, a plug flow reactor or a continuous stirred reactor system operated at a temperature comprised between 70 and 180° C., preferably 90 to 150° C. and at a pressure comprised from 0.01 and 10 bara, preferably between atmospheric pressure and 3 bara.

The alcohol, which is most often an aliphatic alcohol having from 1 to 12 carbon atoms might be withdrawn from the reaction medium in order to increase reaction efficiency. The hydrolysis reaction may be conducted in the presence of a catalyst, which may be lactic acid itself.

The finally recovered lactic acid may be further concentrated and then recycled to the oligomerization reaction, or to the upstage lactic acid production step.

The process of the invention has the unexpected advantage that it can recover all the residues which are mentioned like water, lactic acid oligomers and lactide, that cannot be done in the previous processes, and therefore, the process of the invention enables to reach very weak amount of lost products.

The overall process for producing PLA and taking into account the steps of the present invention to drastically reduce the loss of products while recovering a maximum and recycling the products like water, lactic acid, oligomers, catalytic residues at the different steps may be described in view of FIG. 1 which represent a flow sheet of the process.

An aqueous solution of lactic acid is subjected to water elimination through evaporation. The eliminated water recovered from reactor (20) which contains some lactic acid is then recycled to reactor (20), while the main flow coming out from reactor (20) is sent to the oligomerization reaction in reactor (30). During said oligomerization reaction, some water, lactic acid, which has not oligomerized are withdrawn from reactor (30) and after separation of the water, which is simply purged, the remaining lactic acid is recycled to reactor (20).

The main flow coming out from reactor (30) is sent to the cyclization reactor (40) for the production of a crude lactide stream. From reactor (40), a flow is withdrawn containing the unreacted oligomers, catalytic residues and heavier products, said flow being sent to the trans-esterification reactor (80).

The crude lactide stream resulting from cyclization is then sent to purification of lactide and which is represented by reactors (50), comprising any well known apparatus used for such purification and comprising at least distillation and/or melt crystallization means.

From purification step, represented by reactor (50), the light components lactic acid and water are recovered and recycled to reactor (20), while part of it, which may be up to 100%, is sent to the hydrolysis reactor (90) where lactic acid can act as catalyst of the hydrolysis reaction. Depending on lactic acid concentration in this stream and hydrolysis process efficiency, the minimum content of the light components stream to be sent to the hydrolysis reactor evolves between a few to several tens of percents. On the other hand the heavier components, the impurities and catalytic residues withdrawn from purification step, represented by (50), are recovered and recycled to the trans-esterification reactor (80).

The purified lactide is then sent to ring opening polymerization in reactor (60) and the obtained PLA is purified in a devolatilization reactor (70).

From the devolatilization reactor (70) it is recovered and recycled the non reacted lactide which is withdrawn and recycled partially to lactide purification or directly to the trans-esterification unit (80).

The process of the invention is further described by the following examples which are in no way limitative of the scope of the invention.

EXAMPLES

Example 1

We started with 6,000 Kg of an 88% aqueous solution of lactic acid.

This solution was subjected to water elimination by heating at a temperature of 100° C. and under reduced pressure of 250 mbara.

Water recovered was purged and the lactic acid recovered was recycled to reactor (20).

The concentrated lactic acid (100%) is sent to reactor (30) for oligomerization, which is operated at temperature of 160° C. and at a reduced pressure of 250 and down to 80 mbara, to produce oligomers of lactic acid having a molecular weight of about 950 Dalton (comprised between 900 and 1,000 Dalton.).

From reactor (30) water is withdrawn and purged, while unreacted lactic acid is recovered and recycled to reactor (20).

The oligomers formed in reactor (30) were then sent to the cyclization step in reactor (40).

The cyclization of the oligomers of lactic acid was achieved in the presence of Sn octanoate as catalyst, at a temperature of 250° C. and pressure of 10 mbara and enabled to produce a crude lactide stream.

From reactor (40), the unreacted oligomers, the catalytic residues as well as the heavier components were withdrawn and the withdrawn flow was sent to the trans-esterification reactor (80).

The crude lactide stream coming out from reactor (40) was sent to the purification step of the crude lactide. Said purification comprises, in the present example, melt crystallization means (50), from which the heavy components withdrawn from melt-crystallization means (50) were recovered and sent to the trans-esterification reactor (80).

The obtained lactide was then subjected to ring opening polymerization in reactor (60) at a temperature of 185° C. during 30 minutes in the presence of Sn octanoate and the obtained PLA is purified in a devolatilization reactor (70) from which the non-reacted lactide was removed and recycled to lactide purification. In case of presence of catalytic or other impurities, devolatilization stream can be sent to trans-esterification reactor (80).

We finally recovered PLA with an overall molar yield of 96%.

Example 2

By way of comparison a process has been conducted with the recycling as described in the prior art, meaning at the evaporation step, at the oligomerization and cyclization steps. The overall molar yield obtained in said comparative process was of 78%.

The invention claimed is:

1. An integrated process for the production of polylactide (PLA) comprising the steps of:
   (1) Water evaporation from the lactic acid aqueous solution starting stream;
   (2) Oligomerization of lactic acid and recycle of reaction water and unconverted lactic acid;
   (3) cyclization of the lactic acid oligomers and production of crude lactide and recycle of unreacted monomers, catalytic residues and heavy products;
   (4) Purification of the crude lactide and recycle of lactic acid, water, heavy components, catalytic residues and impurities;
   (5) Ring opening polymerization of the purified lactide and production of PLA;
   (6) Purification of the PLA by devolatilization and recycle of non-reacted lactide;
   wherein
      recycle of step (2) comprises water, which is purged, and lactic acid which is recycled to the water evaporation reactor;
      recycle of step (3) is sent to trans-esterification reactor;
      recycle of step (4) comprising (i) the light components steam, is sent to the water evaporation reactor and/or to the hydrolysis reactor, and (ii) the heavy components stream is sent to trans-esterification reactor;
      recycle of step (6) is sent partially to step (4) and the rest is sent to trans-esterification reactor;
   wherein the light components stream, containing lactic acid and water issued from step (4) is divided into two sub-streams, the first, representing from 10 to 100% by weight of the light components stream, is sent to the hydrolysis reactor while the second, representing from 0 to 90% by weight of the light components stream, is recycled to the water evaporation reactor.

2. Integrated process according to claim 1, wherein the recycles of step (3), the heavy components recycled from step (4) and the recycles of step (6) are collected and sent to trans-esterification reactor to be subject to trans-esterification reaction under a pressure comprised between 1 and 20 bara and at a temperature comprised between 80 and 200° C., and finally the recovery of a stream comprising alkyl lactate which is sent to the hydrolysis reactor.

3. Integrated process according to claim 1, wherein the heavy components recycled from step (4) and the stream of alkyl lactate recovered from trans-esterification reactor are collected and sent to the hydrolysis reactor, to be subject to hydrolysis reaction under a pressure comprised between 0.01 and 10 bara, at a temperature comprised between 70 and 180° C., to recover lactic acid or its derivatives.

4. Integrated process according to claim 3, wherein the stream of alkyl lactate exiting the trans-esterification reactor is separated into two streams through distillation means in order to recover, the first stream containing the light components (lactate, alcohol and the like) to be sent to the hydrolysis reactor and the second stream containing the heavy components (catalytic residues, oligomers and the like) to be recycled to the trans-esterification reactor or purged, said distillation means being operated under a pressure comprised between 0.01 bara and 4 bara, at a temperature comprised between 40 and 180° C.

5. Integrated process according to claim 4, wherein the catalytic residues contained in the purged heavy components are optionally separated and treated before being sent back to trans-esterification reactor, and/or oligomerization reactor, and/or cyclization reactor.

6. Integrated process according to claim 2, wherein the heavy components recycled from step (4) and the stream of alkyl lactate recovered from trans-esterification reactor are collected and sent to the hydrolysis reactor, to be subject to hydrolysis reaction under a pressure comprised between 0.01 and 10 bara, at a temperature comprised between 70 and 180° C., to recover lactic acid or its derivatives.

7. Integrated process according to claim 6, wherein the stream of alkyl lactate exiting the trans-esterification reactor is separated into two streams through distillation means in order to recover, the first stream containing the light components (lactate, alcohol and the like) to be sent to the hydrolysis reactor and the second stream containing the heavy components (catalytic residues, oligomers and the like) to be recycled to the trans-esterification reactor or purged, said distillation means being operated under a pressure comprised between 0.01 bara and 4 bara, at a temperature comprised between 40 and 180° C.

8. Integrated process according to claim 7, wherein the catalytic residues contained in the purged heavy components are optionally separated and treated before being sent back to trans-esterification reactor, and/or oligomerization reactor, and/or cyclization reactor.

* * * * *

UNITED STATES PATENT AND TRADEMARK OFFICE
CERTIFICATE OF CORRECTION

| | |
|---|---|
| PATENT NO. | : 9,777,109 B2 |
| APPLICATION NO. | : 15/102812 |
| DATED | : October 3, 2017 |
| INVENTOR(S) | : Christian Penu et al. |

It is certified that error appears in the above-identified patent and that said Letters Patent is hereby corrected as shown below:

In the Claims

Claim 1, Line 23, delete "steam" and replace with --stream--

Signed and Sealed this
Twenty-sixth Day of December, 2017

Joseph Matal
*Performing the Functions and Duties of the*
*Under Secretary of Commerce for Intellectual Property and*
*Director of the United States Patent and Trademark Office*